_US006119695A_

United States Patent [19]
Augustine et al.

[11] Patent Number: 6,119,695
[45] Date of Patent: Sep. 19, 2000

[54] AIRWAY DEVICE WITH PROVISION FOR LATERAL ALIGNMENT, DEPTH POSITIONING, AND RETENTION IN AN AIRWAY

[75] Inventors: Scott Douglas Augustine, Bloomington; Randall Charles Arnold, Minnetonka; Thomas Wayne McGrail, Chaska, all of Minn.

[73] Assignee: Augustine Medical, Inc., Eden Prairie, Minn.

[21] Appl. No.: 09/199,909

[22] Filed: Nov. 25, 1998

[51] Int. Cl.$^7$ .................................................. A61M 16/00
[52] U.S. Cl. .............................. 128/207.15; 128/207.14
[58] Field of Search ................ 128/207.14, 207.15, 128/200.26; 604/96

[56] References Cited

U.S. PATENT DOCUMENTS

| | | | |
|---|---|---|---|
| 4,351,342 | 9/1982 | Wiita et al. | 128/349 B |
| 4,509,514 | 4/1985 | Brain | 128/207.15 |
| 4,976,261 | 12/1990 | Gluck et al. | 128/207.15 |
| 4,995,388 | 2/1991 | Brain | 128/207.15 |
| 5,038,766 | 8/1991 | Parker | 128/200.26 |
| 5,122,125 | 6/1992 | Deuss | 604/282 |
| 5,241,956 | 9/1993 | Brain | 128/207.15 |
| 5,259,371 | 11/1993 | Tonrey | 128/200.26 |
| 5,303,697 | 4/1994 | Brain | 128/200.26 |
| 5,305,743 | 4/1994 | Brain | 128/207.15 |
| 5,355,879 | 10/1994 | Brain | 128/207.15 |
| 5,443,063 | 8/1995 | Greenberg | 128/207.15 |
| 5,477,851 | 12/1995 | Callaghan et al. | 128/207.15 |
| 5,494,029 | 2/1996 | Lane et al. | 128/207.15 |
| 5,513,627 | 5/1996 | Flam | 128/200.26 |
| 5,584,290 | 12/1996 | Brain | 128/207.15 |
| 5,623,921 | 4/1997 | Kinsinger et al. | 128/200.26 |
| 5,632,271 | 5/1997 | Brain | 128/207.15 |
| 5,655,528 | 8/1997 | Pagan | 28/207.14 |
| 5,720,275 | 2/1998 | Patil et al. | |
| 5,743,258 | 4/1998 | Sato et al. | |
| 5,896,858 | 4/1999 | Brain | 128/207.15 |
| 5,937,859 | 8/1999 | Augustine et al. | 128/207.15 |
| 5,983,897 | 11/1999 | Pagan | 128/207.15 |

FOREIGN PATENT DOCUMENTS

| | | |
|---|---|---|
| 0 389 272 A2 | 3/1990 | European Pat. Off. . |
| 0 533 371 A2 | 9/1992 | European Pat. Off. . |
| 478958 | 1/1938 | United Kingdom . |
| WO 95/32754 | 12/1995 | WIPO . |
| WO 97/12640 | 4/1997 | WIPO . |
| WO 97/12641 | 4/1997 | WIPO . |
| WO 98/16273 | 4/1998 | WIPO . |
| WO 98/23317 | 6/1998 | WIPO . |
| WO 98/50096 | 11/1998 | WIPO .......................... A61M 16/00 |

OTHER PUBLICATIONS

International Search Report for PCT/US97/16838.

*Primary Examiner*—Aaron J. Lewis
*Assistant Examiner*—Teena Mitchell
*Attorney, Agent, or Firm*—Gary Care Ware Freidenrich

[57] ABSTRACT

An airway device for sealing against the laryngeal opening includes an air tube with proximal and distal ends and a sealing member attached to the distal end. The sealing member has a distal portion with a pair of opposing lateral flanges for engaging the cricoid cartilage to laterally align the sealing member with respect to the laryngeal inlet. The sealing member has a compressible anterior surface that contacts and seals against the laryngeal inlet. A tubular extension of the distal end of the air tube projects through and beyond the compressible anterior surface. The sealing member has a pronounced sigmoid shape having a lower section which, together with the tubular extension, creates a hook that provides an end point for accurate cephalad-caudad depth placement of the sealing member against the rim of the laryngeal inlet.

21 Claims, 14 Drawing Sheets

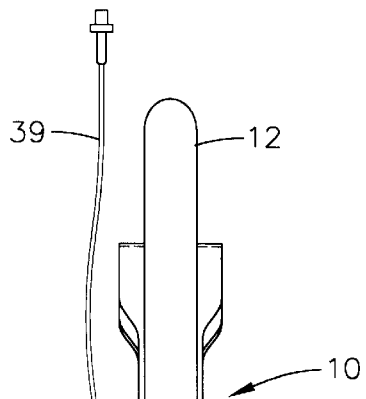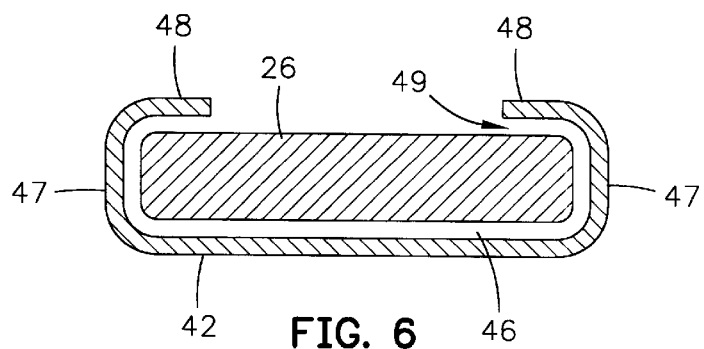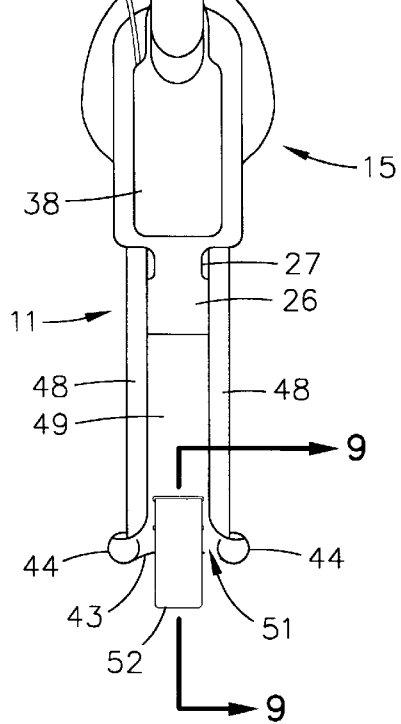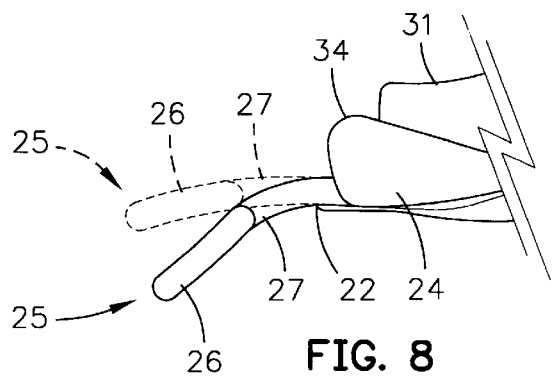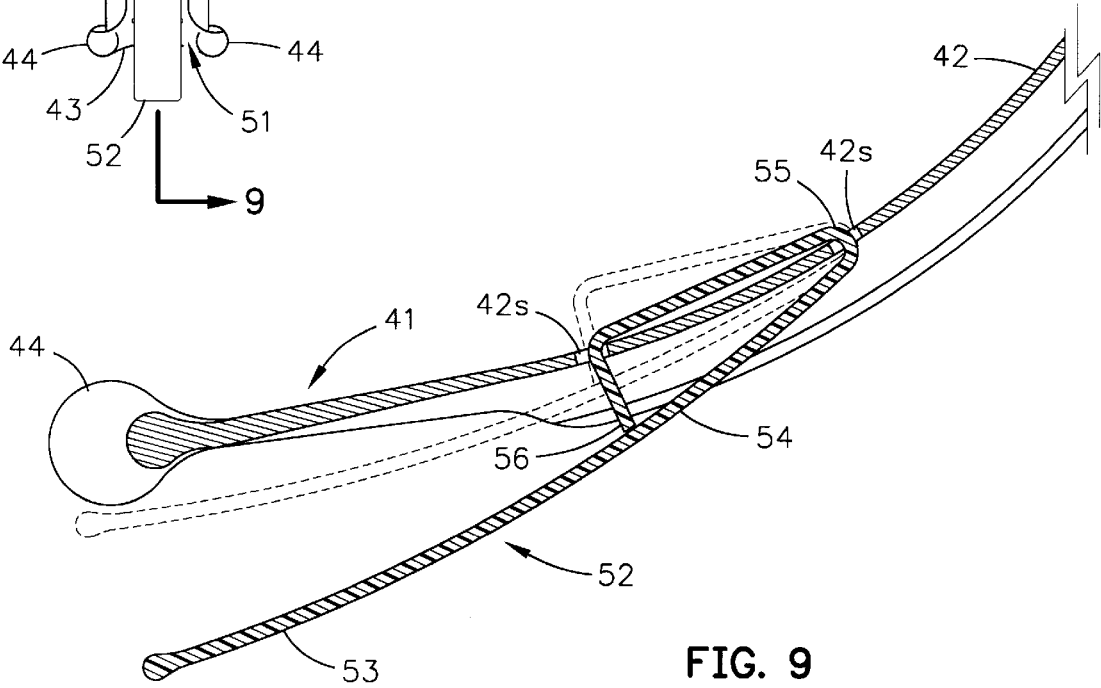
FIG. 6
FIG. 7
FIG. 8
FIG. 9

AIRWAY DEVICE WITH PROVISION FOR LATERAL ALIGNMENT, DEPTH POSITIONING, AND RETENTION IN AN AIRWAY

CROSS-REFERENCE TO RELATED APPLICATION

This application contains subject matter that is related to the following patent applications:

U.S. patent application Ser. No. 08/730,791, filed Oct. 16, 1996, for LARYNGEAL AIRWAY DEVICE, now U.S. Pat. No. 5,938,859, issued Aug. 17, 1999;

U.S. patent application Ser. No. 08/885,682, filed Jun. 30, 1997, for LARYNGEAL AIRWAY DEVICE;

PCT Application No. US97/16838, filed Sep. 24, 1997, for LARYNGEAL AIRWAY DEVICE; and U.S. patent application Ser. No. 09/199,540, filed on Nov. 25, 1998, for AIRWAY DEVICE WITH PROVISION FOR COUPLING TO AN INTRODUCER

BACKGROUND OF THE INVENTION

1. Field of the Invention

This invention is concerned with the management of a human airway in order to control respiration. More particularly, the invention concerns a device that brings an airway tube reliably and safely into communication with the laryngeal opening, the upper end of the trachea, which is the breathing passageway that leads to the lungs. The device seats in the throat immediately adjacent the laryngeal opening, tensions and erects the laryngeal opening, and seals with it to provide a channel through the airway tube for artificial ventilation of the lungs. In particular, the invention concerns a device that can accurately position itself laterally with respect to the laryngeal opening, that can accurately position itself in depth with respect to the larynx, and that can retain itself in position during operation.

2. Description of the Related Art

An airway device facilitates ventilation of the lungs of a person. The purpose of such a device is to provide an air pathway from an external air source, through the mouth, throat, and trachea, to the lungs. Additionally, some airway devices provide a seal with the throat of a person, which allows positive pressure ventilation and which may also prevent the leakage of stomach contents into the trachea (aspiration).

It is useful to divide airway devices into two categories: those that pass through the vocal chords and are commonly referred to as "tracheal tubes", and those that lodge in the throat, above the vocal chords, and are commonly referred to as "airways". We shall limit "airway" to refer to a device that provides a fluid pathway from outside the mouth of a person to a location above the vocal chords.

In the variety of airway devices that are available, some merely support the tissue of the pharynx (throat), particularly the tongue, creating a passageway so that air can pass by and into the pharyngeal space toward the laryngeal opening, which is the opening into the voice box. Other airway devices include a tube that provides an air channel to a location near the laryngeal opening. Still other airway devices add a sealing means to the distal end of the tube in order to provide some degree of sealing between the tube and the airway of the person.

A laryngeal mask is an example of a sealing airway device. U.S. Pat. Nos. 4,509,514; 4,995,388; and 5,355,879 are descriptive of a laryngeal mask. A laryngeal mask includes an inflatable doughnut-shaped balloon which, when inflated, circles the laryngeal opening and creates a fluid seal between the outside of the inflated balloon and the tissues in the pharyngeal structures of the throat that surround the larynx.

Another sealing airway device, described in U.S. Pat. No. 5,513,627, includes an inflatable balloon fixed on the distal end of a tracheal tube that is inserted into and inflated within the trachea, forming a seal against the interior walls of the trachea.

In the first three cross-referenced patent applications, all assigned to the assignee of this application and incorporated in their entirety by this reference, a sealing member is mounted near the distal end of an airway tube to seal directly with the rim of the laryngeal opening, portions of the epiglottis, and the sidewalls of the larynx. This unique airway creates a fluid seal directly with the larynx.

Airway devices that seal with the larynx or pharyngeal structures surrounding the larynx need to be accurately positioned with respect to the larynx. However, it is common knowledge to the clinician that it can be very difficult to accurately position an airway device with respect to the anatomy of the larynx, which can be highly variable and extremely flexible.

Positioning of an airway device with respect to the larynx is difficult in both the lateral axis and the cephalad-caudad axis (which is also called the "depth" axis). Further, once correctly seated, it can be very difficult to maintain an airway device in the correct position. Maintaining the correct position is important for several reasons. First, proper ventilating of the patient is critical to patient safety and care. Second, anesthetic gases are intended to be delivered to the patient's lungs and a poorly aligned airway could result in the gases being introduced into the patient's esophagus or into the operating room environment. Finally, should there be any regurgitation of contents from the patient's stomach, the airway seal must be secure to prevent the contents from entering the patient's lungs.

The larynx is made of several flexible cartilages and membranes which span the cartilages. The laryngeal opening looks like the open end of a pipe that has been cut off at an angle of roughly 45°. The acute, angled, pointed edge of the laryngeal opening is formed by the epiglottis and positioned on the anterior (front) side of the throat (also called the pharynx). The flexible epiglottis is a cartilage that is highly variable in shape and size. The epiglottis can easily be bent backward to cover the laryngeal opening if pressure or a stimulus is applied on its anterior side. The obtusely angled posterior edge of the laryngeal opening is formed by the two arytenoid cartilages. The arytenoideous muscle, which is stretched between the arytenoid cartilages, forms the base of the inter-arytenoid notch. The sidewalls of the laryngeal opening are formed by the ary-epiglottic folds. These are flexible, compressible membranes, stretching from the arytenoid cartilages posteriorly to the epiglottis anteriorly. The larynx then, is a flexible, collapsible structure that stands up like an angled pipe in the hollow of the pharyngeal space. Manifestly, the laryngeal opening, especially on its anterior side is not a firm or consistent structure on which to position an airway device.

All of the sealing devices presently align themselves laterally with respect to the larynx by filling the pharyngeal space (throat) with an inflatable balloon or a resilient foam pad. The assumption is that the larynx lies in the midline of the pharynx and therefore an inflated balloon will center the airway in the pharyngeal space, which should approximately align with the laryngeal opening. Generally this assumption holds for pharyngeal airway devices. Pharyngeal airway devices loosely surround the laryngeal opening and form a seal on the pharyngeal structures. Therefore, precise orientation with the laryngeal opening is not necessary. On the other hand, laryngeal airway devices such as those described and illustrated in the incorporated patent applications, require very precise orientation with the laryngeal opening if they are to form a dependable seal. Lateral alignment with the pharyngeal structures is not accurate enough for reliable lateral alignment with the laryngeal opening.

Accordingly, there is a need for an airway device that can accurately position itself in the lateral dimension with respect to the laryngeal opening.

Anterior to the larynx is the vallecula, which is the angle formed between the anterior side of the epiglottis and the tongue. The vallecula has served as a positioning point for the introduction of laryngoscopes and other introducers. However, the vallecula is not a practical end-point for positioning laryngeal airway devices at or within the laryngeal opening, because it is outside of the laryngeal opening, on the opposite side of the epiglottis from the laryngeal opening.

On the posterior side of the larynx is the hypo-pharynx, which is the smooth lower part of the throat that leads to the esophagus and stomach. There are no protuberances or pockets on the hypo-pharynx that can serve as an end-point on which to position an airway device with respect to the depth axis of the laryngeal opening.

Similarly, the hypo-pharynx on both sides lateral to the larynx describes a substantially smooth taper down to the esophagus, without protuberances or pockets. Therefore there is no good end-point laterally, on which to seat an airway at or in the laryngeal opening.

Accordingly there is a need for an airway device that can accurately position itself along a depth axis (cephalad-caudad) with respect to the larynx.

Assuming correct positioning of an airway device on a lateral axis and on a depth axis with respect to the laryngeal opening, it becomes necessary to retain the airway device in that correct position, accurately oriented with the laryngeal opening over a prolonged period of time. Again, the anatomy of the throat is not helpful in this respect. The hypo-pharynx is substantially funnel-shaped and it would seem obvious that a funnel-shaped airway device, inflated within the funnel-shaped hypo-pharynx would naturally seek to eject itself from the seated position.

Airway devices that seal against the angled laryngeal opening are inherently unstable. The sealing surface of the device must be angled to match the natural angle of the laryngeal opening. Abutting these two angled surfaces also creates an unstable situation in which the airway device may be naturally ejected from the correct position.

The angle of the vallecula between the anterior side of the epiglottis and the tongue is oriented opposite the direction necessary to retain an airway device in position with respect to the laryngeal opening. Accordingly the vallecula does not afford an anchoring or retention site.

The tongue is highly flexible and has no protuberances which can serve as anchors on which to retain an airway device. Most airways present smooth surfaces in order to minimize trauma to the delicate tissues of the throat, larynx, and trachea. The smooth flexible surface of the tongue cannot interact with the smooth surface of an airway device to provide any appreciable amount of "grasping". Therefore, the tongue would seem not to present an opportunity for airway device retention.

The pharynx and hypo-pharynx on the posterior and lateral sides of the larynx also present smooth tissue surfaces without protuberances or angles which can serve to retain an airway device.

At present, an airway device is most frequently retained in position by simply taping the air tube of the device to the face of a person. This is not an ideal or accurate solution to the problem of positioning because the tape may become loose or dislodged, because the skin of the face is very mobile, and because the proximal end of the tube (where the tape is usually applied) is not consistently or precisely oriented with respect to the distal end of the tube, where the airway device is located. Moreover, the shape of the tube may change during airway device operation, further changing the relationship between its proximal and distal ends. The net result may be a movement of the distal end of the tube, which can dislodge the airway device from its correct position.

Accordingly, there is a need for an airway device which can retain itself naturally and accurately in a correct position with respect to the laryngeal opening.

SUMMARY OF THE INVENTION

The invention is a sealing laryngeal airway device that forms a fluid seal against the rim of the laryngeal opening, that is, against the larynx itself. The invention provides for accurate lateral positioning of a device with respect to the laryngeal opening. The invention provides for accurate depth positioning of the device with respect to the laryngeal opening. The invention also provides for retention of the device, when positioned.

Lateral positioning is provided by orientation of the laryngeal airway device against the ring-shaped cricoid cartilage which is located at the base of the angled laryngeal opening.

The laryngeal airway device includes a sealing member attached near the distal end of the airway and having an anterior surface with a generally sigmoid shape. The lower (distal) part of the sealing member engages in the throat anatomy between the larynx and the posterior pharynx, stabilizing the laryngeal airway device. The distal end of the air tube protrudes through and slightly beyond the anterior surface distally. The combination of the protrusion and the lower part of the sigmoid-shaped anterior surface of the sealing member creates a "hook" that accurately positions the laryngeal airway device along the depth axis of the laryngeal opening.

The anterior surface of the sealing member has an anterior-proximal edge, which forms an upper rim of the sealing member. The upper rim has an edge surface. When the tongue of a patient is relaxed, it drapes over the upper rim and hangs down over the edge surface, trapping the edge surface within a fold of tongue tissue and retaining the airway device in its correct position.

BRIEF DESCRIPTION OF THE DRAWING

FIG. 6 is a sectional drawing taken along line 6—6 of FIG. 5.

FIG. 7 is a plan view of the posterior side of the laryngeal airway device of FIG. 1 coupled to the introducer of FIG. 4.

FIG. 8 is a magnified side view of a portion of the distal end of the laryngeal airway device of FIG. 1.

FIG. 9 is a magnified side sectional view of the distal end of the introducer taken along line 9—9 of FIG. 7.

DETAILED DESCRIPTION OF THE PREFERRED EMBODIMENTS

The invention is described in terms of a laryngeal airway device, that is, an airway device designed to form a fluid seal against and within the rim of the laryngeal opening. Because the seal is against and within the rim of the larynx itself, and not with the pharyngeal structures surrounding the larynx, positioning must be very accurate. The invention provides for accurate positioning of a laryngeal airway device. It should be noted however that the mechanisms and techniques that position a laryngeal airway device according to this invention could also work well with a pharyngeal airway device. Therefore, the invention may be applied generally to an airway device.

Figure 1:
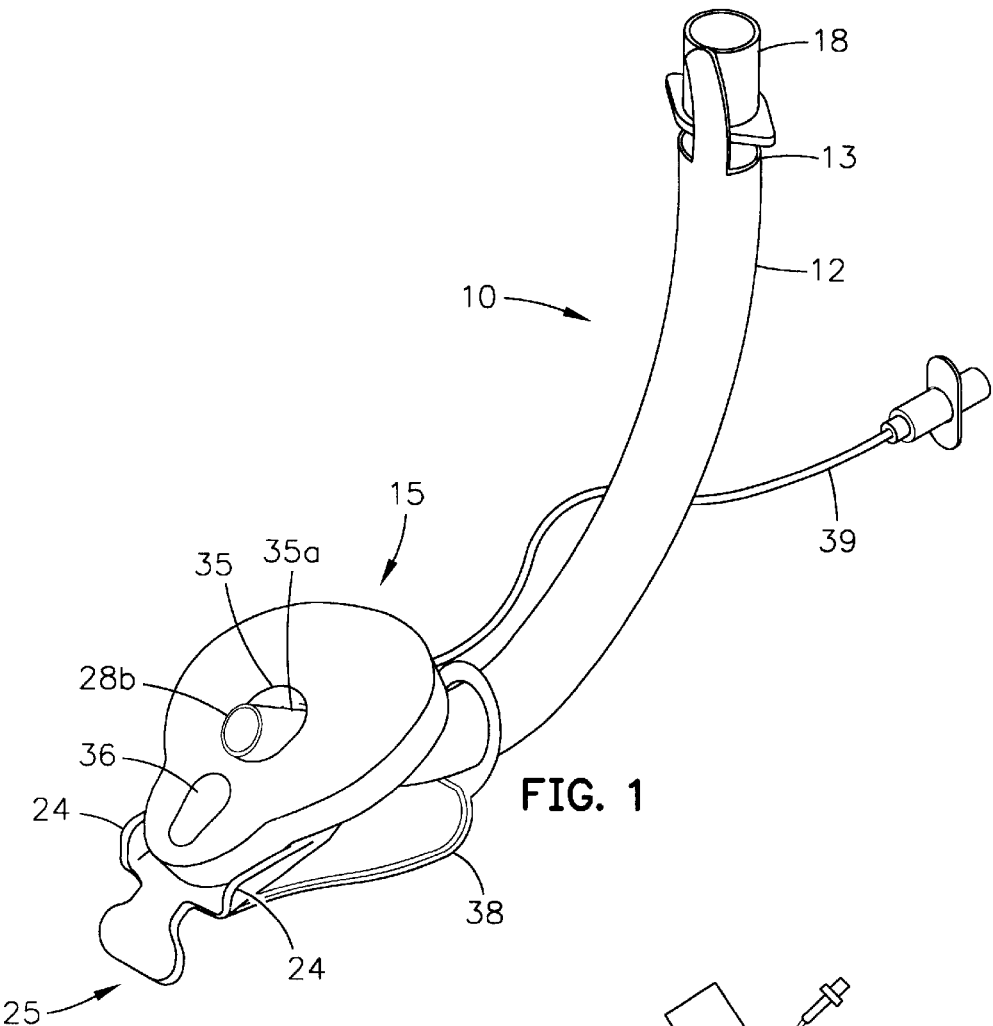
FIG. 1 is a perspective view of a laryngeal airway device according to this invention.
Figure 3:
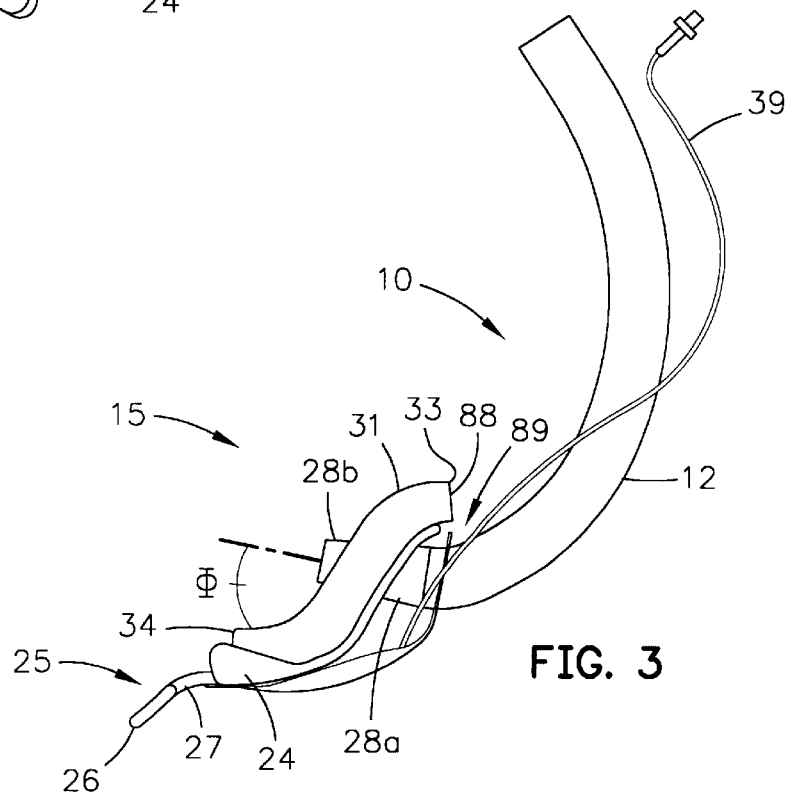
FIG. 3 is a side elevation view of the laryngeal airway device of FIG. 1.
Figure 2:
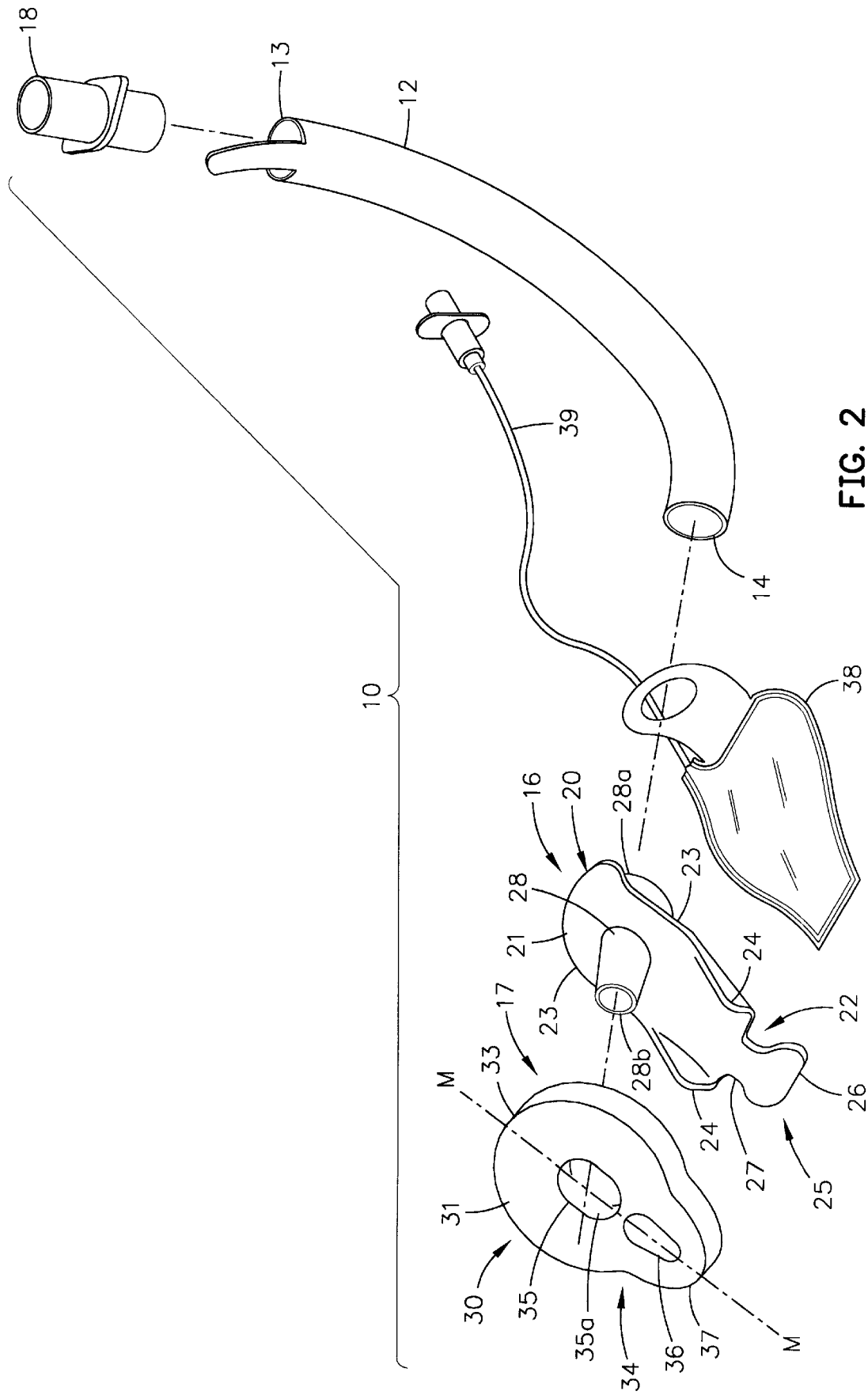
FIG. 2 is an exploded view of the laryngeal airway device of FIG. 1.
Figure 4:
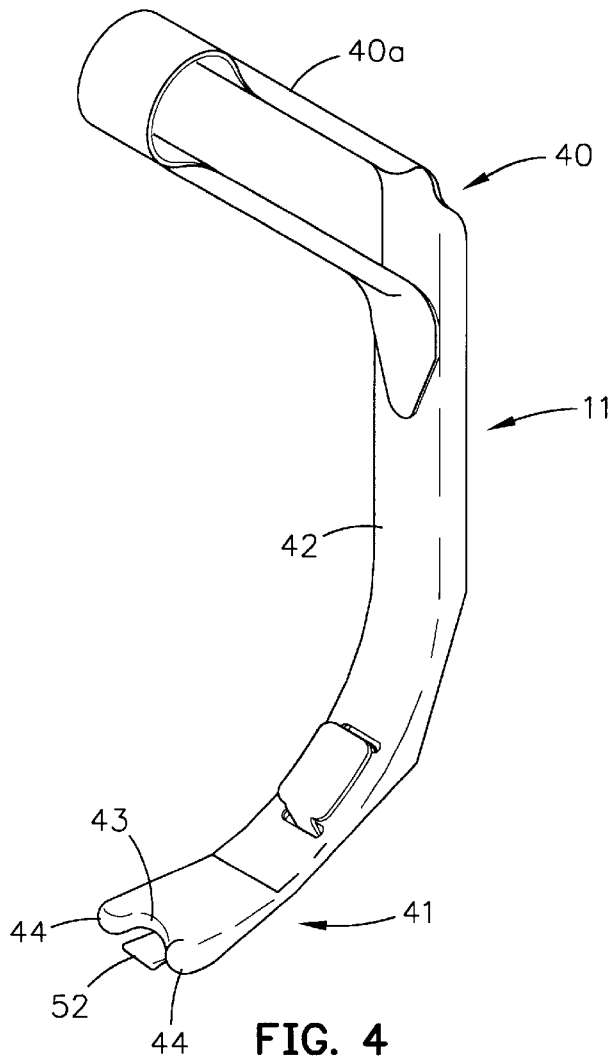
FIG. 4 is a perspective view of an introducer that may be used with the laryngeal airway device of FIG. 1.
Figure 5:
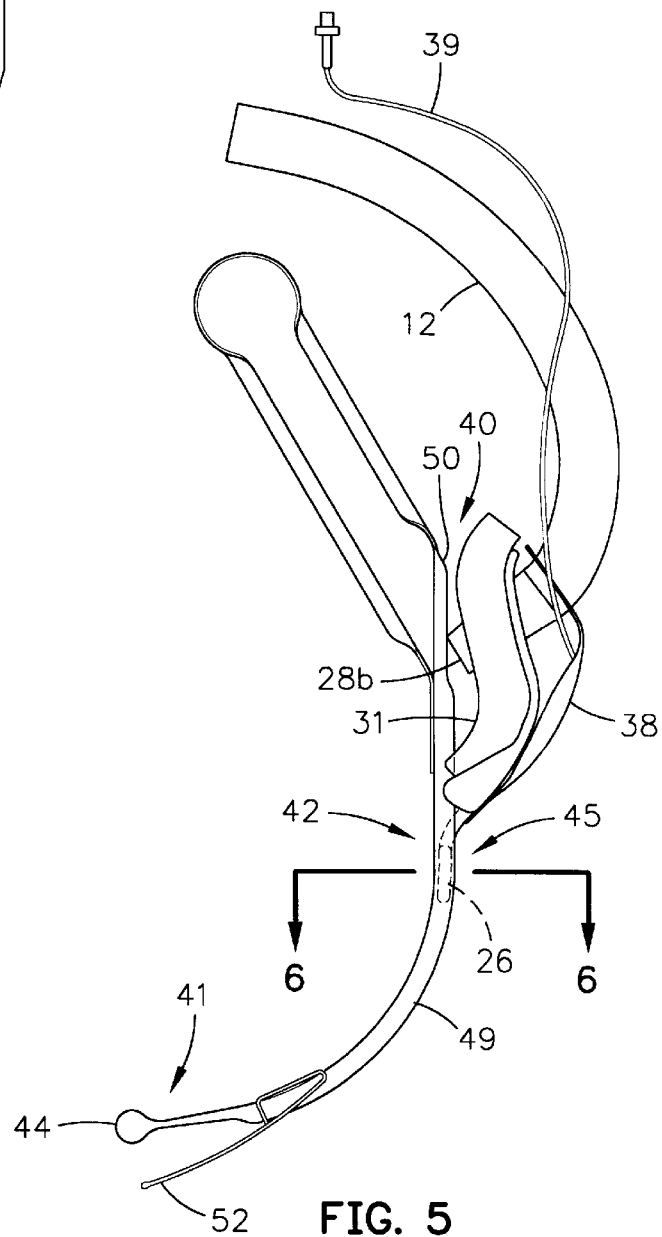
FIG. 5 is a side elevation view of the laryngeal airway device of FIG. 1 coupled to the introducer of FIG. 4.

FIGS. 1, 2 and 3 illustrate an example of a laryngeal airway device 10 that incorporates features of our invention. The laryngeal airway device 10 includes a curved, flexible air tube 12 having first (proximal) and second (distal) ends 13 and 14, respectively. Preferably the tube 12 has a curved shape that conforms to the contour of the back of the tongue. A connector 18 is attached to the proximal end 13 to connect the tube to a ventilating means, which is not shown. A sealing member 15 is attached to the tube 12 near its distal end 14. The sealing member 15 includes a support member 16 and a compressible foam pad 17.

In more detail, the support member 16 has an upper (proximal) end 20 and an anterior support surface 21, a distal end 22, and sides 23. The anterior support surface 21 has a generally sigmoid shape in a longitudinal section. In a lateral section, the shape of the anterior support surface 21 is generally flat, although there may be some variation to accommodate design, manufacturing, or operational considerations. The lower (distal) third of anterior support surface 21 extends to the distal end 22. Laterally of the distal end 22 are a pair of opposing cricoid retainers embodied as lateral flanges 24 that rise upwardly along the sides 23 from the distal portion of the anterior support surface 21. A coupler or tracking mechanism is provided in the distal portion of the support member 16. In these figures, this mechanism is embodied as a flexible flange 25 that extends forwardly of the distal end 22. The flexible flange 25 may perform one, or two useful functions: esophageal tracking and coupling to an introducer. Both functions are described below. The structure of the flexible flange 25 includes a tab 26 that is connected to the distal end 22 by a pedestal 27. The lateral extent of the tab 26 at its widest section is preferably less than the width of the distal end 22 of the support member 16. The pedestal 27 is narrower than both the tab 26 and the distal end 22. The air tube 12 is enabled to project through the anterior support surface 21 of the support member 16 by a tubular, "snout-like" extension 28 that is a hollow cylinder having proximal and distal ends 28a and 28b, respectively. The tubular extension 28 is fixed to the support member 16 and the distal end 14 of the air tube 12 is received and fixed in the proximal end 28a of the tubular extension 28. The tubular extension 28 has a generally conical-like shape, with the narrower radius found at the distal end 28b and the wider radius at the proximal end 28a. The tubular extension may also be entirely cylindrical, or partially tubular, resembling a hood. Manifestly, the tubular extension 28 may be a shaped, molded portion of the air tube 12, or a piece that is separate altogether from the air tube 12 but attached to the distal end 14. The tubular extension 28 may also be slit to allow passage of an endotracheal tube.

The compressible pad 17 preferably has a pear-like shape with an upper, or proximal portion 30 and a lower or distal portion 34. The upper portion 30 is relatively wider than the lower portion 34. The compressible pad has an anterior surface 31. The upper portion 30 includes a hole 35 defining a passageway 35a in the sealing member 15 that is centered in the upper portion 30 and on a longitudinal midline M of the pad 17. The hole 35 opens through the anterior surface 31 and the passageway 35a extends through the pad 17, aligned longitudinally with the distal end 14 of the air tube 12. The tubular extension 28 is disposed in the passageway 35a. A slot, elongated hole, notch, or depression 36 is provided in the anterior surface 31, preferably centered on the midline M, and positioned between the hole 35 and a distal end 37 of the compressible pad 17. The length of the compressible pad 17 that extends from a proximal end 33 to the distal end 37 is such that, when the pad 17 is joined to the support member 16, the distal end 37 of the pad is positioned between the lateral flanges 24, set back from the distal end 22. This leaves open a channel defined laterally between distal portions of the lateral flanges 24 and longitudinally between the distal end 37 of the compressible pad 17 and the distal end 22 of the support member.

Preferably, and for illustration and example only, the support member 16 is a flexible plastic part that may be fabricated by molding 85 durometer PVC material. In this case, the air tube 12 should be made of somewhat stiffer material, for example 90 durometer plastic. The anterior support surface 21 has the generally sigmoid shape described above. Alternate embodiments of the anterior support surface 21 may be substantially flat, convex, or concave in longitudinal section.

The compressible pad 17 is preferably made by molding a closed cell foam having a density of about seven pounds to make the pad soft and conformable. When the compressible pad 17 is integrated with the support member 16, its anterior surface 31 takes on the sigmoid shape of the support member's anterior support surface 21. That is, the anterior surface 31 has a sigmoid contour imposed on it in a longitudinal section, but is substantially flat in opposing lateral sections that extend from the midline M laterally to the sides of the pad 17.

The sealing member 15 may be fabricated by molding or die cutting the elements 16 and 17 and then combining them into a unitary structure by attaching the pad 17 to the anterior surface 21 of the support member 16 by gluing, heat bonding, or ultrasonic bonding, by some form of riveting, by a combination of any of these methods, or by any other equivalent that will yield an integrated, unitary structure in which the foam pad 17 has a soft, compressible characteristic, while the support member 16 is relatively more rigid than the pad 17, yet with a flexibility in one or more of its elements that allows bending during use.

Although the sealing member 15 is illustrated and described as comprising two parts, it should also be evident that, with a selection of materials and methods, this member can comprise one part with two portions in which the materials and structures of one portion transition continuously or abruptly to the materials and structures of the other portion.

As is best seen in FIG. 3, an inflatable balloon 38 is disposed on the posterior side of the support member 16, extending generally between the proximal end 28a of the tubular extension 28 and the distal end 22 of the support member 15. A small tube 39 is provided for inflating the balloon 38. The balloon 38 may be provided to compensate for unusual variations in airway anatomy. It will not be necessary to inflate the balloon 38 in all patients in order to effect an airway seal.

Refer now to FIGS. 4, 5, 6 and 7 for an understanding of an introducer with which the laryngeal airway device of FIGS. 1–3 may be used. This explanation is for illustration only. Indeed it is contemplated that a sealing airway device according to this invention could be used with or without an introducer. The introducer, indicated by generally 11, is a relatively stiff plastic or metal blade-like device having a straight portion and a curved portion. Preferably, though not necessarily, the shape of the introducer 11 may be that of a capital "J". A first (proximal) end 40 of the introducer 11 transitions to a generally elongate proximal section with an anterior surface 42 and a posterior side 45. A handle 40a is provided at the proximal end 40. A second (distal) end 41 terminates the sharp "hook-shaped" portion of the "J"-shape of the introducer. Preferably, the introducer 11 is substantially flattened in cross-section. Preferably, although not necessarily, the distal end 41 preferably includes an indentation 43 on either side of which is a rounded protuberance 44. The indentation 43 is designed to accommodate the midline hyo-epiglottic ligament, while the protuberances 44 are designed to engage under the hyoid bone for accurate positioning of the introducer 11. These means of positioning have been described in U.S. Pat. Nos. 4,832,020 and 5,042,469, which are owned by the assignee and incorporated by this reference.

Referring to FIGS. 4, 5, 7, and 9, an epiglottic engager, disposed on the distal end 41 of the introducer, is shown. Preferably, this is a moveable epiglottic engager 52 that is pivotally attached to the distal end 41 of the introducer 11. As best seen in FIG. 9, the epiglottic engager 52 has an elongate flattened forward section 53 that transitions to a closed triangular section 54 with an apex 55 and an opposing base 56. The apex 55 and base 56 are received in slots 42s through the posterior side 45 near the distal end 41 of the introducer 11. The forward section 53 projects beyond the base 56 toward the distal end 41 of the introducer 11. As best seen in FIG. 9, the moveable epiglottic engager 52 can pivot between a fully extended position indicated by the solid lines and a closed position indicted by the dashed lines. Preferably the engager is made of the same material as the blade. However, it is contemplated and may be desirable, that the moveable engager be a different material, such as plastic. It should also be understood that the engager could be a removable component to accommodate substitution of differently dimensioned engagers.

FIGS. 1, 5, 6 and 7 illustrate elements of the device 10 and the introducer 11 that permit these two elements to operate cooperatively in tracking or guiding the device 10 into alignment with the laryngeal opening. The flexible flange 25 on the distal end 22 of the sealing member 15 may be coupled to a track 46 formed on the posterior side of the introducer 11. As shown best in FIGS. 5–7, the track 46 includes two opposing slide rails that are generally "U"-shaped and are formed by upwardly-extending wall portions 47, which extend longitudinally on the posterior side 45. The wall portions 47 transition to medially-extending sections 48. There is a gap 49 between the medially-extending sections 48.

The device 10 is coupled to the introducer 11 by orienting the compressible anterior surface 31 of the sealing mechanism toward the posterior side of the introducer 11 and inserting the flange 25 between the "U"-shaped slide rails on the posterior side of the introducer 11 where the rails begin at 50 near the proximal end 40. The opening 49 captures the edges of pedestal 27, while the tab 26 of the flange 25 is retained between the slide rails. When the device is pushed toward the distal end 41 of the introducer 11, the air tube 12 is rotated to place the distal end 28b of the tubular extension 28 toward the posterior side, within the opening 49 between the slide rails. When pressure directed toward the sealing member 15 is applied on the tube 12, the device is advanced, sealing member 15 first, along the posterior side of the introducer 11 towards its distal end 41. When the flange 25 emerges from between the slide rails at the opening 51 where the medially-facing portions 48 of the slide rails taper toward the vertical portions 47, the flange 25 is released from the rail track of the introducer 11 and the device 10 is uncoupled from the introducer 11.

Of course if a sealing airway device according to the invention is not intended to be used with an introducer, the flange 25 may be altered in form if esophageal tracking is desired; or, it may be omitted altogether.

In this exemplary construction of the device 10, and as illustrated in FIG. 8, the material of which the support member 16 is made imparts a flexibility that permits the flange 25 to rotate between a first position indicated by the solid lines in FIG. 8 and a second position that is indicated by the dashed line in FIG. 8. In the first position, the device 10 is not coupled to the introducer 11. However, in the second position, the flange 25 has been engaged between the slide rails of the introducer 11 and the device 10 has been advanced to the point just before the flange 25 is released.

Lateral and Cephalad-Caudad Depth Positioning

Figure 10A:
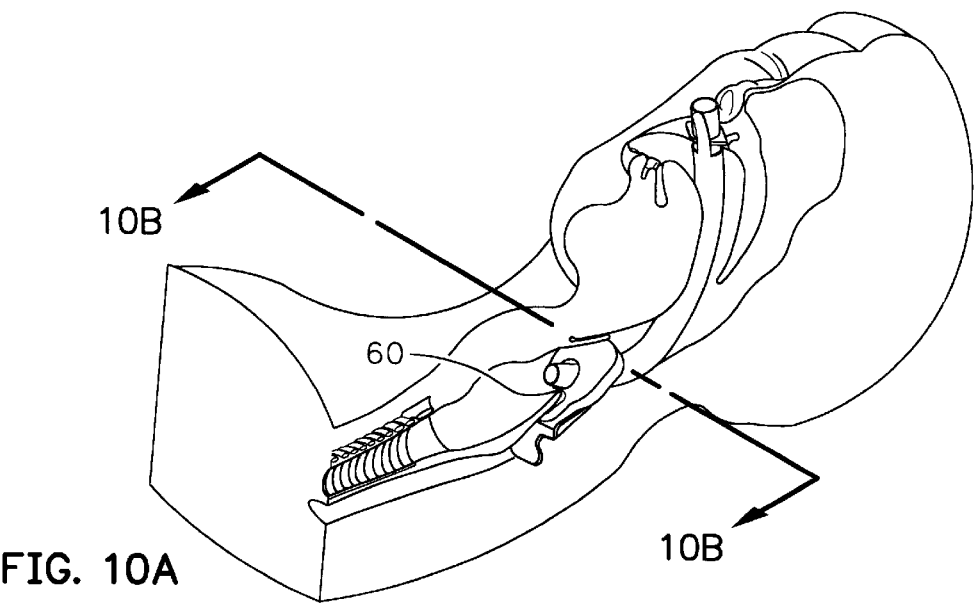
FIG. 10A is a partial cutaway perspective view of the anatomy of the throat with the laryngeal airway device of FIG. 1 positioned in the anatomy.

FIG. 10A is a cutaway perspective view of the anatomy of a throat with the laryngeal airway device 10 seated against the laryngeal opening 60.

Figure 10B:
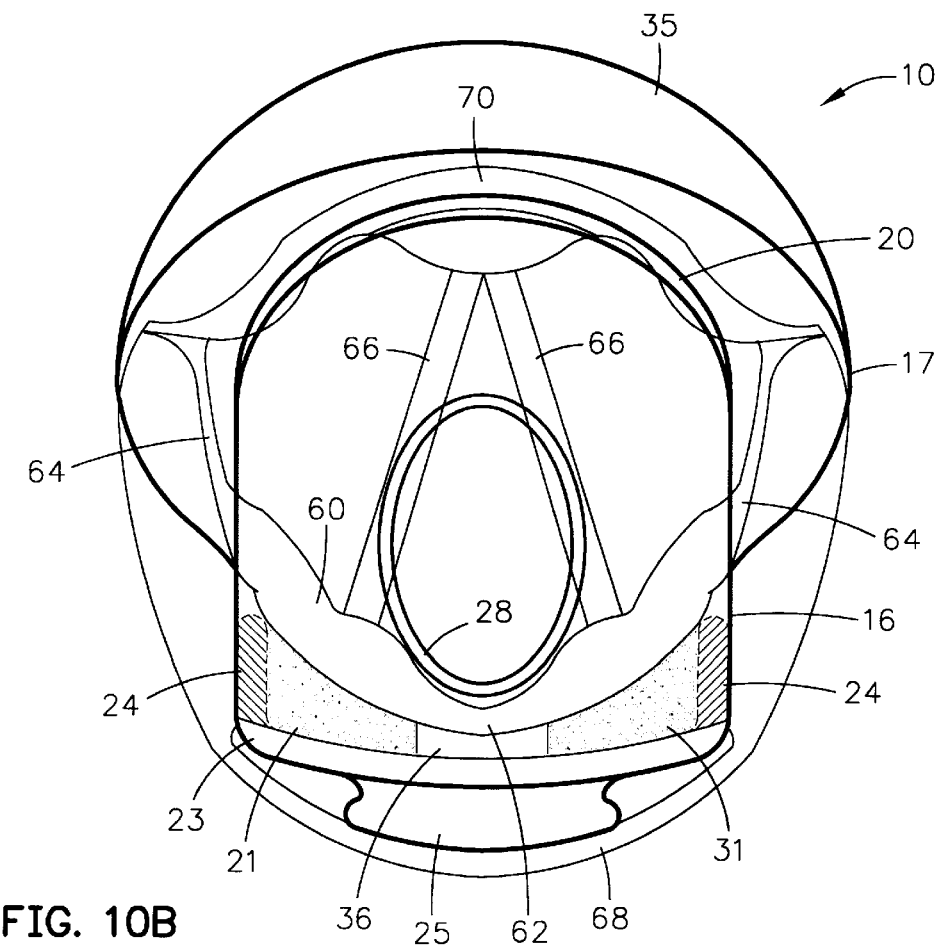
FIG. 10B is a schematic lateral cross-sectional representation of the anatomy of the throat taken along line B—B of FIG. 10A.

FIG. 10B is a schematic lateral cross-sectional representation of the laryngeal anatomy taken along line B—B of FIG. 10A. The direction of the view is toward the throat, from behind the sealing member 15. The view is schematic and imaginary, assuming that the sealing member is substantially transparent, with the outlines of its major components—the support member 16 and the compressible pad 17—indicated by heavy lines. In these views, the rim of the laryngeal opening is indicated by reference numeral 60, the inter arytenoid notch by reference numeral 62, the aryepiglottic folds by 64, the vocal chords by 66, the esophagus by 68, and the epiglottis by 70.

With respect to lateral positioning, the two opposing, substantially parallel lateral flanges 24 extend anteriorly and seat on each side of the cricoid cartilage which is disposed toward the bottom of the larynx, distal to the rim 60. When the cricoid cartilage is cradled between the lateral flanges 24, it is contained within the channel defined between the distal portions of these elements, which assures lateral alignment of the tubular extension 28 within the laryngeal opening with respect to the vocal chords 66. FIGS. 1, 2, and 3 illustrate the lateral flanges 24 as being located on the lateral edges 23 of the anterior supporting surface 21. In this illustration, the lateral flanges 24 extend for only part of the length of the sides; however, they may extend for shorter, or longer distances along the sides. In a side elevation view, the ridges may assume many shapes including, but not limited to, wall-like, rounded, square or rectangular, triangular, truncated triangular, or a combination of these shapes or any shapes that are equivalent and that serves the purpose of lateral retention. When viewed elevationally from the front of the support member 16, the lateral flanges 24 may have many shapes including, but not limited to, a wall, a tab, or a cylinder.

In considering cephalad-caudad positioning, refer to FIGS. 1, 3, and 10. Recall the sigmoid shape of the anterior support surface 21, which is imposed on the anterior surface 31 of the compressible pad 17. The lower portion of the sigmoid that is described by the lower or distal portion 34 of the compressible pad is designed to seat between the larynx and the posterior pharynx, stabilizing the device 10. The lower portion of the support member 16, that is, the portion generally just above the distal end 22 to the end of the flange 25, is preferably angled posteriorly when molded. The posterior angle assures that the flange 25 and distal end 22 will be applied directly against the posterior wall of the pharynx when the airway 10 is advanced into its position of use. The midportion of the sigmoid shape is angled to abut the angled rim of the laryngeal opening 60, along the ary-epiglottic folds. The upper portion of the sigmoid shape is flattened to seal against the posterior side of the epiglottis, within the laryngeal opening. The "snout-like" tubular extension 28 protrudes through the hole 35, beyond the anterior surface 31, into the laryngeal opening 60. This snout helps create a fluid seal against the larynx by holding the laryngeal tissues out of the distal opening 28b, to prevent obstruction of air flow. As stated above, the tubular extension 28 is preferably shaped like a truncated cone, with its wide base attached to the distal end 14 of the air tube 12. The narrow distal end 28b is opened to allow air flow and it is this part that penetrates most deeply into the laryngeal opening 60.

Accurate cephalad-caudad depth placement is provided by the combination of the "snout-like" distal end 28b of the tubular extension 28 and the lower part 34 of the anterior surface 31 of the sealing member. This combination creates a "hook". The angle $\Phi$ (FIG. 3) between the distal end 28b of tubular extension 28 and the lower anterior surface portion 34 is preferably an acute angle, greater than 0° and less than 90°. The base of the notch 62 formed between the arytenoid cartilages is made of the arytenoidous muscle overlaying the cricoid cartilage. These structures are very firm and assure a positive end-point when contacted with a longitudinal force. The hook described by the acute angle $\Phi$ is designed to catch on the cartilage and muscle between the arytenoid cartilages, on the posterior edge of the laryngeal opening. With reference to the "cut pipe" analogy described above, the hook described by the angle $\Phi$ engages over the posterior rim of the laryngeal opening, which is the obtuse angled edge of the rim. With the distal end 28b of the tubular extension 28 lodged inside the laryngeal opening, the hook cannot slip out distally or become displaced laterally when longitudinal pressure is applied to the airway. The arytenoid depression 36 and the anterior surface 31 assists in this positioning by receiving small corniculate tubercles that are on the posterior side of the larynx and that are near the arytenoid notch. The tubercles are received in the depression 36, and assist in positioning the laryngeal airway device 10 longitudinally in the laryngeal opening.

Referring once again to FIGS. 10A and 10B, the cephalad-caudad positioning of the laryngeal airway device 10 may be understood. As shown in this figure, the inter arytenoid notch 62 is positioned between the tubular extension 28 and the distal portion 34 of the compressible pad 17. Although not shown in this view, the distal end 28b of the tubular extension 28 is located above the vocal chords 66. In addition, the arytenoid depression 36 has received the forward portion of the inter arytenoid notch 62 that includes the corniculate tubercles. This provides space in which the tubercles can be received, which enables the posterior side of the inter arytenoid notch to relax somewhat and move with the bottom portion of the tubular extension 28.

Retention

In FIG. 3, there is shown an edge surface 88 on the proximal edge 33 of the compressible pad 17 and a surface 89 that extends from the proximal end 28a of the tubular extension 28 across the distal end 14 of the tube 12. The edge surface 88 receive the tissues on the back portion of the tongue when the sealing member 15 has been advanced to seal against the laryngeal opening with lateral and depth positioning as described above. At this location, the back portion of the tongue relaxes, draping over the edge surface 88 of the proximal edge 33 and hanging down onto and around the surface 89. The rough texture of the surface of the tongue prevents the compressible material at the edge surface 88 from easily sliding across the surface of the tongue. This retains the airway in tight approximation with the larynx by anchoring it with the base of the tongue. The edge surface 88 that is presented by the structure of the distal portion of the laryngeal airway device 10 capitalizes on the flexibility of the tongue to capture the airway at the proximal edge 33 the contact between the anchored base of the tongue and the edge surface 88 retains the edge 33 and prevents the airway 10 from being ejected from its correct positioning against the rim of the laryngeal opening.

Operation

The operation of the laryngeal airway device will now be explained with reference to FIGS. 11–18. This explanation presumes that the sealing device according to this invention is to be used with an introducer such as that illustrated in FIG. 4. Of course, this is not intended to so limit the use of the invention.

Figure 11:
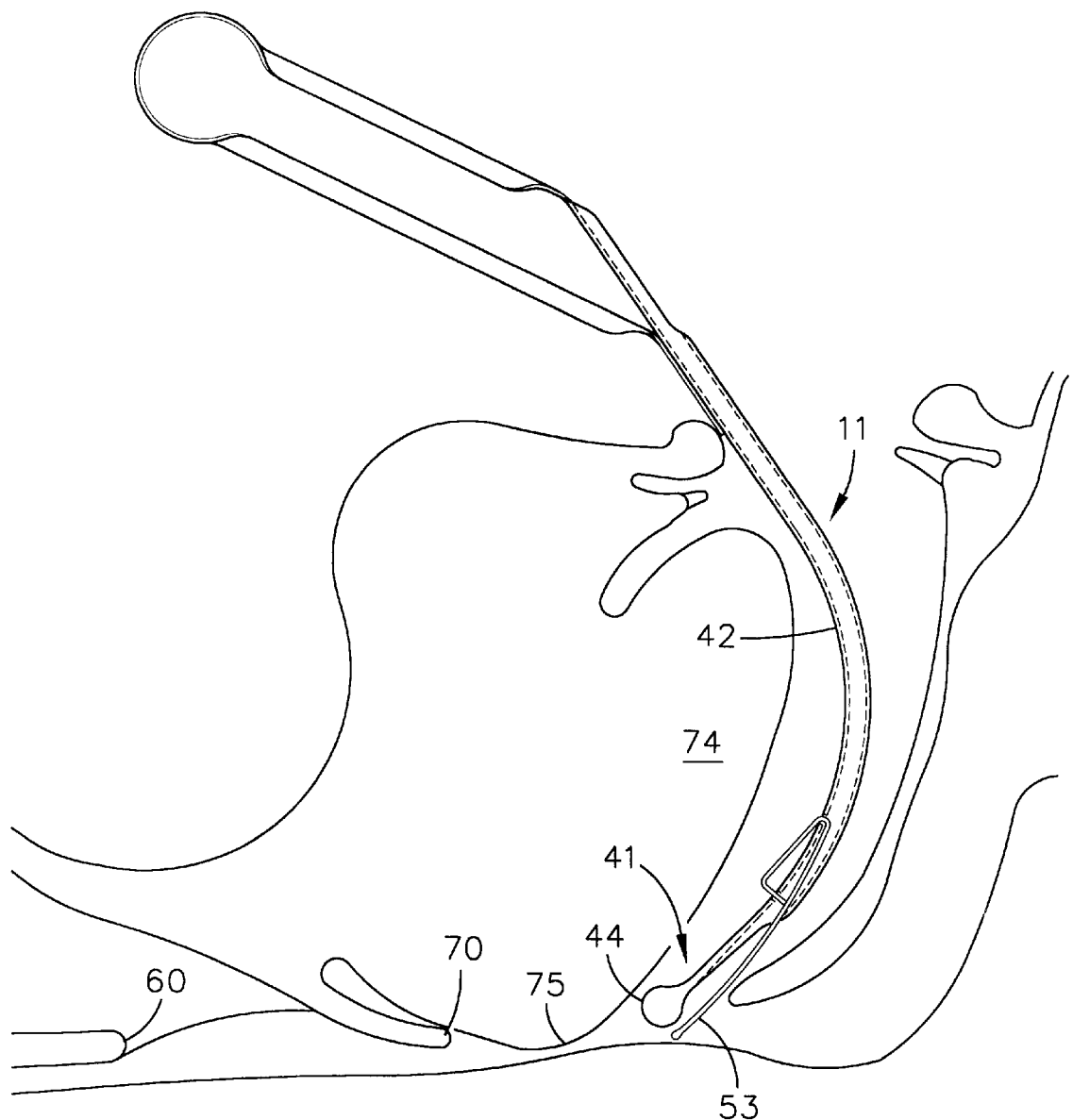
FIGS. 11–14 are schematic side cross-sectional representations of the anatomy of the throat showing the operation of the introducer of FIG. 4.
Figure 12:
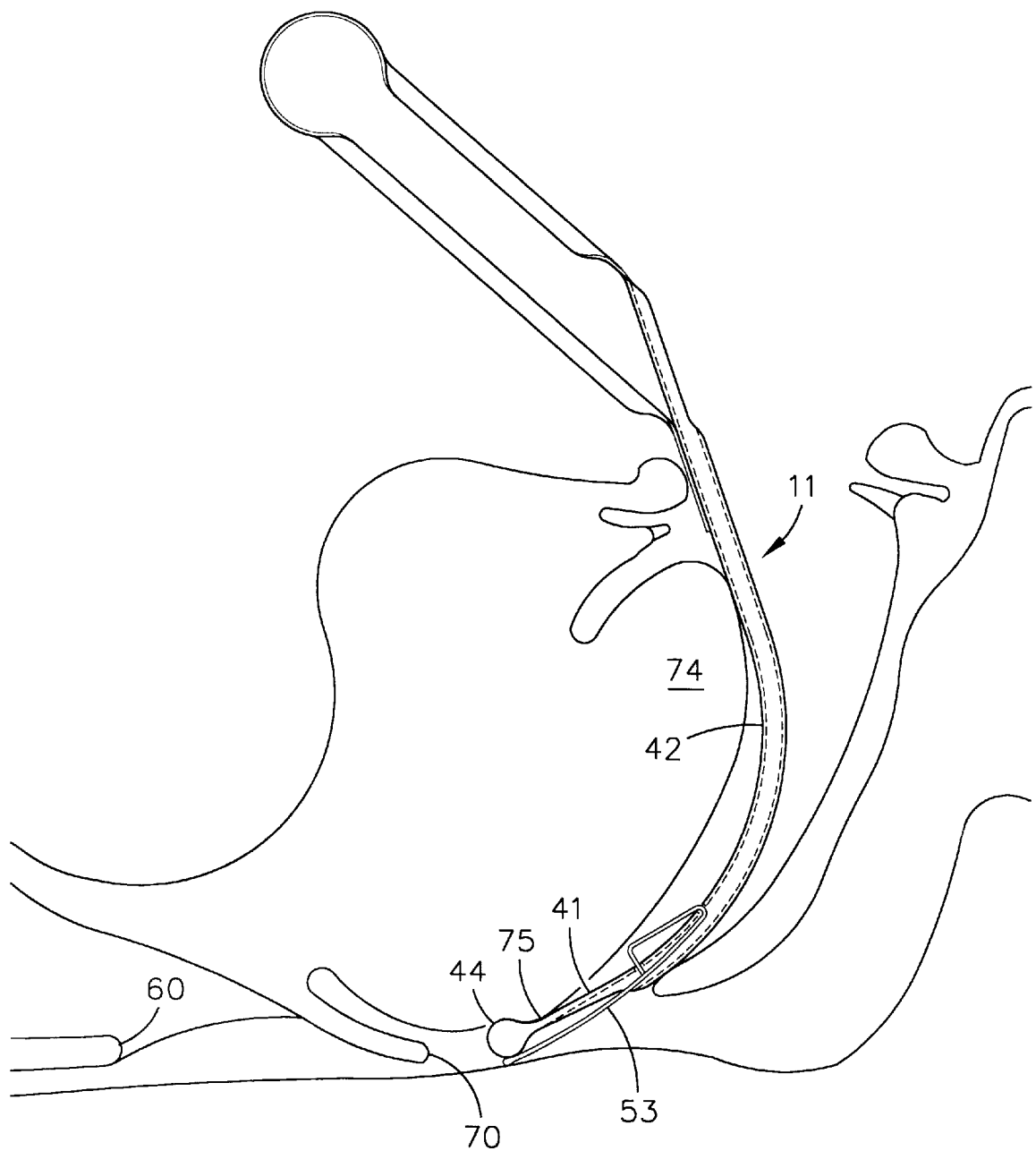
Figure 13:
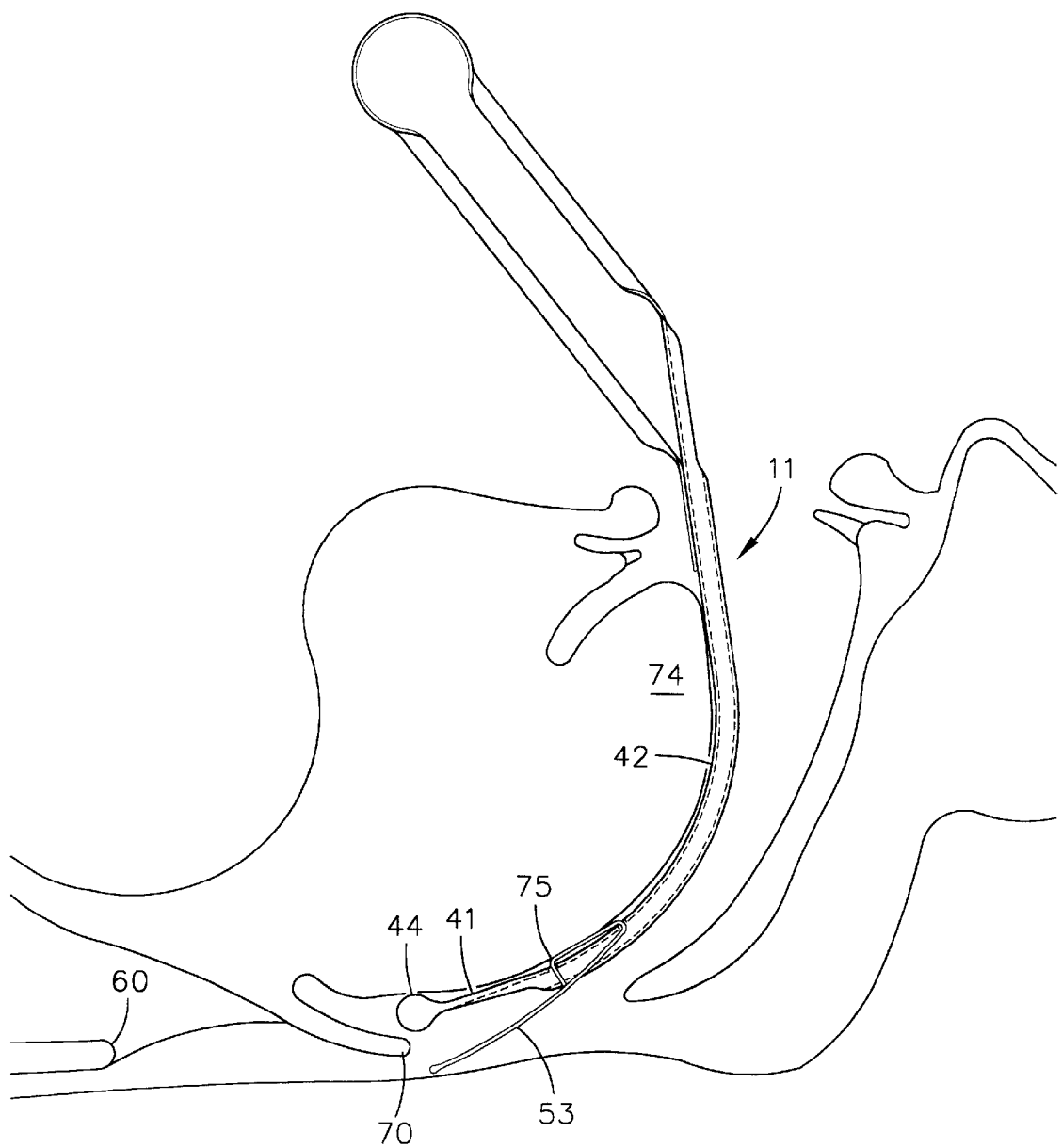
Figure 14:
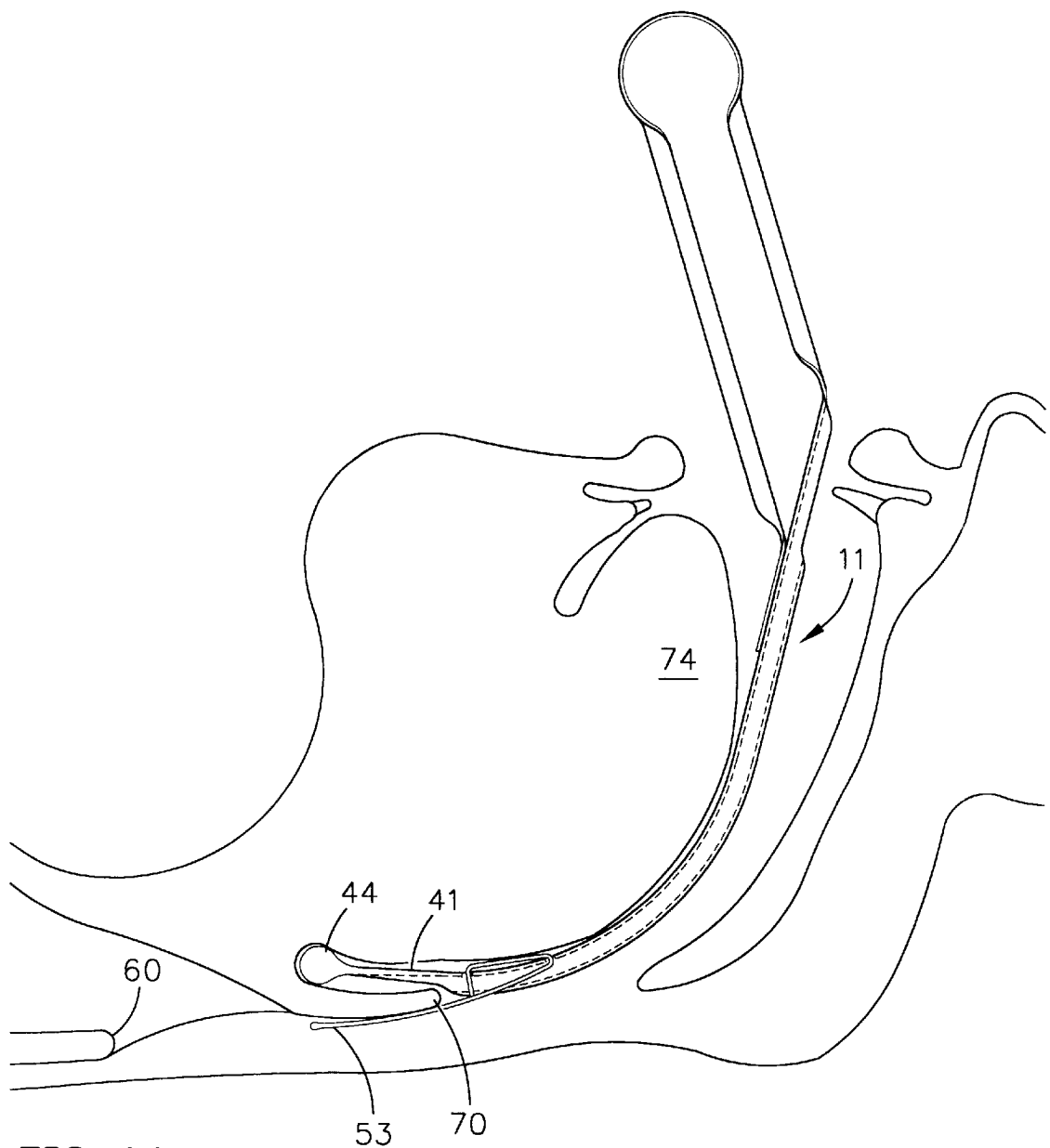
Figure 15:
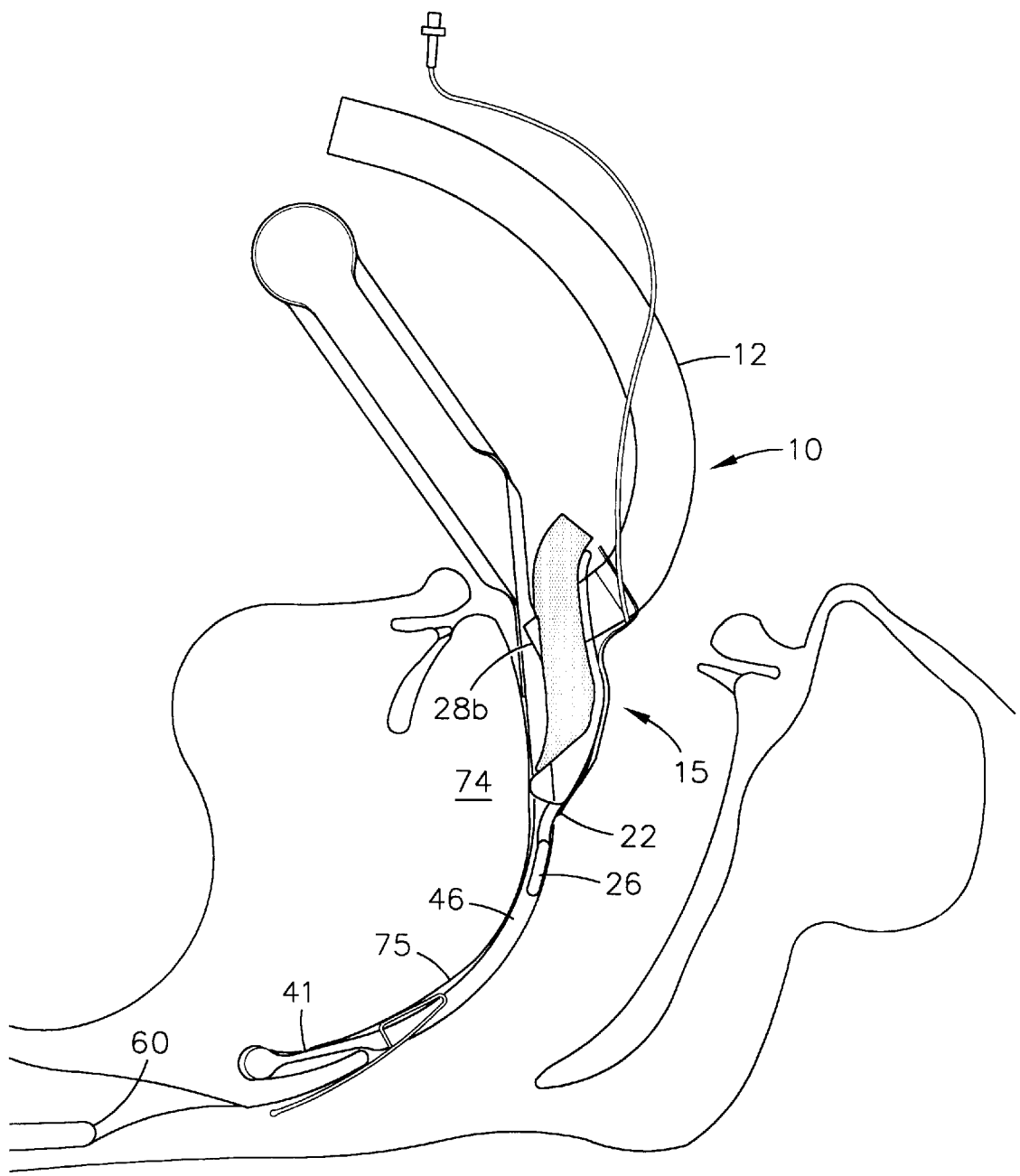
FIGS. 15–18 are schematic side cross-sectional representations of the anatomy of the throat showing the introduction and positioning of the laryngeal airway device of FIG. 1.
Figure 16:
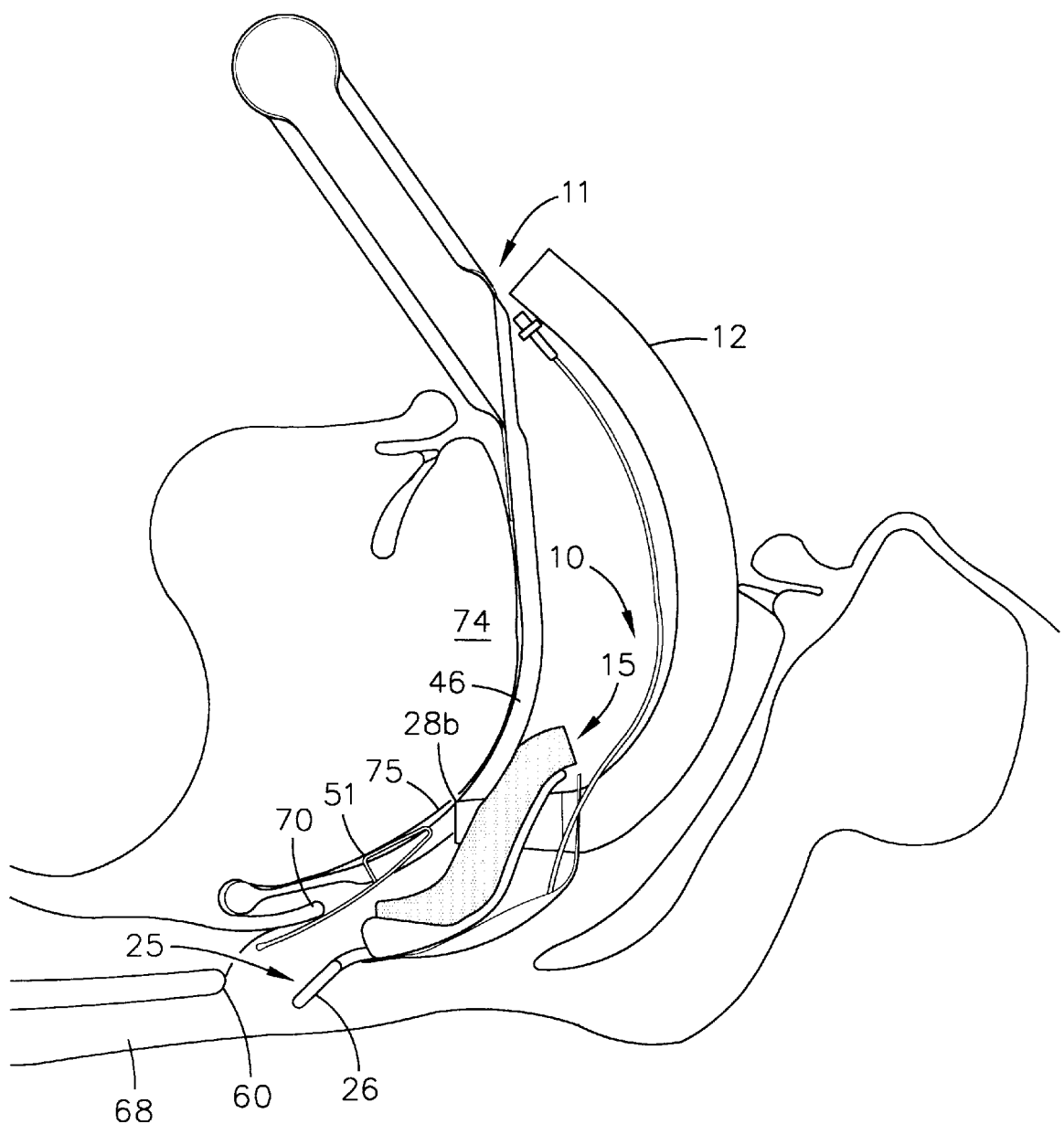
Figure 17:
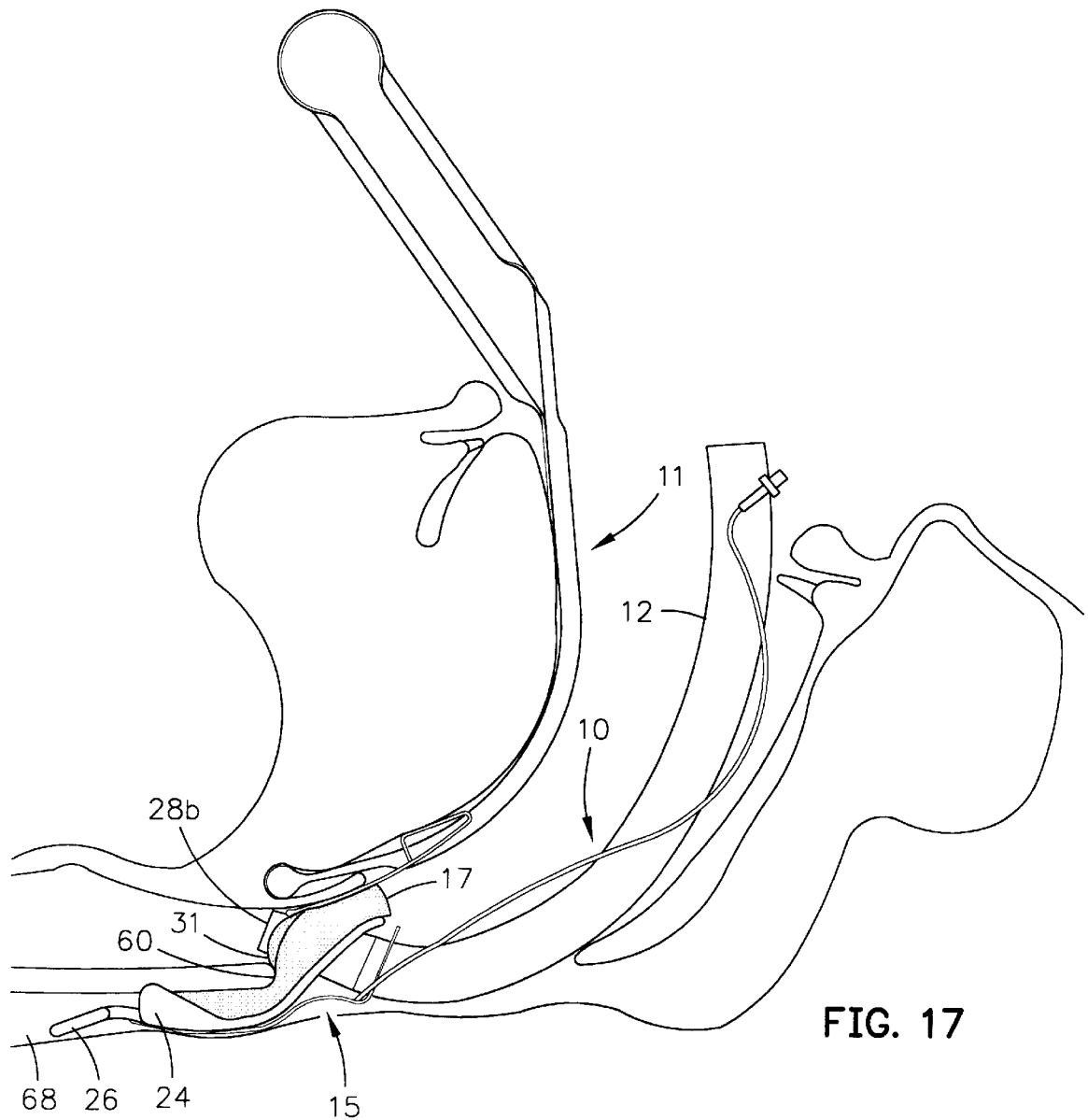
Figure 18:
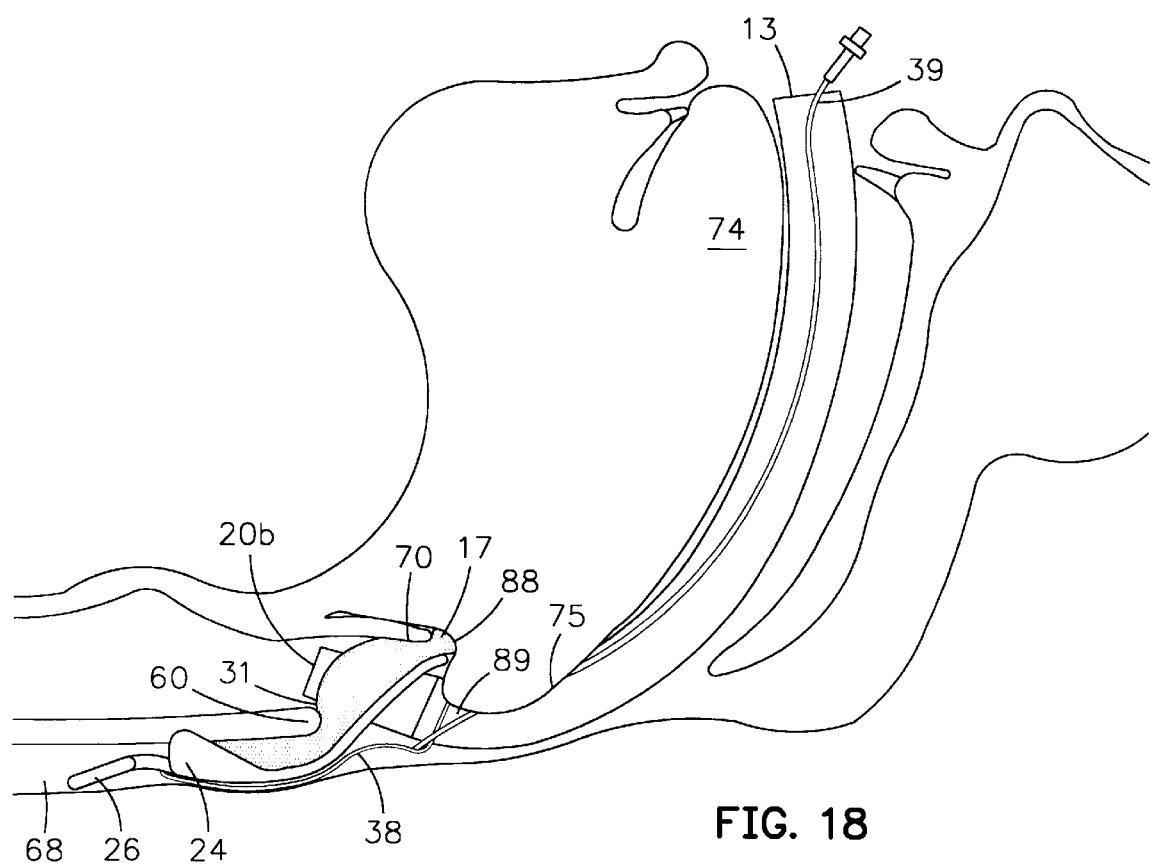

Initially, in FIG. 11, the introducer 11 is inserted, distal end 41 first, through the mouth, traversing the tongue 74 where, in FIG. 11, one of the rounded protuberances 44 is shown approaching the sharp curvature 75 at the back of the tongue. As the distal end of the introducer 11 advances, the flattened forward section 53 of the epiglottic engager 52 is rotated toward the posterior side 45 near the distal end 41 by contacting the back of the throat. In FIG. 12, as the distal end 41 of the introducer 11 passes the sharp curve 75 at the back of the tongue 74, the narrow dimensions of the throat force the structure of the distal end 41 against the back of the tongue 74, lifting the lower tissues of the tongue away from the epiglottis 70. At this point, the flattened forward section 53 of the epiglottic engager 52 is fully rotated toward the distal end 41, between the rounded protuberances 44. In FIG. 13, the introducer 11 is pulled upwardly as it is advanced into the throat, further raising the tissue at the base of the tongue 74 and widening the throat, allowing the flattened forward section 53 of the epiglottic engager 52 to pivot away from the distal end 41 toward the back of the throat. As the distal end 41 of the introducer 11 is advanced to the position shown in FIG. 14, the epiglottis 70 is trapped between the distal end of the introducer 11 and the flattened forward section 53 of the epiglottic engager 52. This retains the tip of the epiglottis 70 upwardly, keeping it out of the space in the throat through which the sealing member of the laryngeal airway device must pass. At this point, the indentation 43 of the distal end 41 of the introducer has received the hyoepiglottic ligament, while the protuberances 44 have been engaged under the hyoid bone to position the introducer 11. In FIG. 15, the laryngeal airway device 10 has been coupled to the introducer 11, with the tab 26 engaged in the track 46. The sealing member 15 is oriented as described above. The laryngeal airway device 10 is advanced along the introducer 11 over the tongue toward the curve 75 at the back of the tongue 74. In FIG. 16, the laryngeal airway device 10 has been advanced to the point where the flange 25 has emerged from the opening 51 at the distal end of the track 46. As the distal end of the laryngeal airway device 10 is advanced further into the throat, the flange 25 springs back to its first position with the tab 26 angled posteriorly toward the back of the throat. At this position, it can perform esophageal tracking. Referring to FIGS. 17 and 18, as the laryngeal airway device 11 is advanced further into the throat, it eventually seats against the rim 60 of the laryngeal inlet, with 25 the distal end 28*b* of the tubular extension 28 extending within the laryngeal inlet and the anterior surface 31 of the compressible pad 17 engaging and sealing against the rim 60, and extending partly into the laryngeal opening in the vicinity of the distal end 28*b*. At the same time, the distal end of the sealing member 15 has tracked down the back of the throat with the tab 26 of the flange 25 tracking toward the esophagus 68. At this point, the above-described features of the laryngeal airway device have aligned and positioned it laterally and along the depth axis of the larynx. Now, the introducer 11 is withdrawn, leaving the laryngeal airway device 10 seated. Withdrawal of the introducer causes the tongue to drape down over the edge surface 88 and the surface 89 which retains the laryngeal airway device in the manner described above.

Clinical experience has shown the inventors that optimal lateral positioning with the laryngeal airway device 10 can be accomplished with a specific maneuver. Once the device 10 is positioned, with the flange 25 located between the larynx and the posterior wall in the pharynx in the upper reaches of the esophagus 68, the proximal end 13 of the laryngeal airway device 10 is grasped. The laryngeal airway device 10 is pulled very slightly out of the mouth against the tension of the tongue and then pushed back in. This maneuver is known as the "Arnold maneuver". The device 10 is not pulled so far out as to cause disengagement with the epiglottis 70 but merely to partially disengage the anterior surface 31 from the rim 60 of the laryngeal inlet. When the device 10 includes the distal end 28*b*, the Arnold maneuver disengages the tip of the distal end 28*b* from an arytenoid cartilage that may be obstructing the rim 60 of the laryngeal opening. On reinsertion, the distal end 28*b* is unobstructed and lies within the laryngeal opening defined by the rim 60. The Arnold maneuver in conjunction with a device 10 that includes the lateral flanges 24 or their equivalent has been shown to dependably orient the device 10 in the lateral dimension with respect to the larynx. If the device 10 includes the snout like distal end 28*b*, the Arnold maneuver dependably places the distal end 28*b* within the laryngeal opening defined by the rim 60 and clears tissue that may obstruct airflow.

If necessary to achieve a desired level of positive pressure, the seal that the laryngeal airway device makes with the laryngeal inlet may be assisted by inflation of the balloon 38 through the tube 39. This may follow the Arnold maneuver, if indicated. Inflation of the balloon 38 will rotate the sealing member anteriorly with respect to the laryngeal opening, further tensioning the opening and further urging the anterior surface of the compressible pad into sealing engagement against the opening.

Alternate Embodiments

The positioning and tracking features of the laryngeal airway device of this invention may be implemented in many ways. Some of the alternative configurations of the lateral flanges 24, the tubular extension 28, and the arytenoid depression 36 have been discussed above.

Figure 19A:
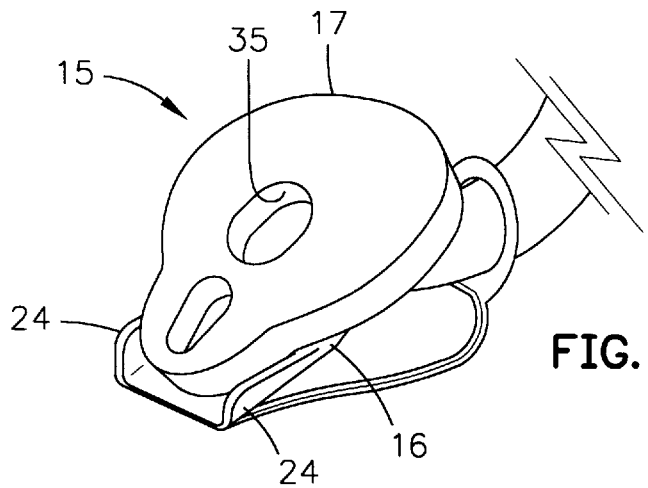
FIGS. 19A, 19B and 19C illustrate some alternate embodiments of features of the laryngeal airway device.
Figure 19B:
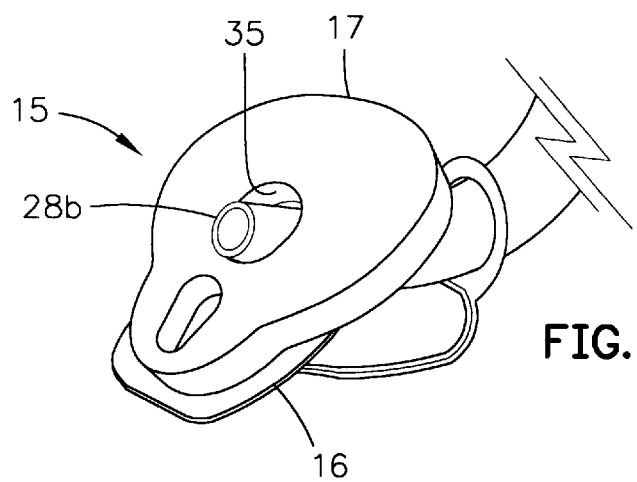
Figure 19C:
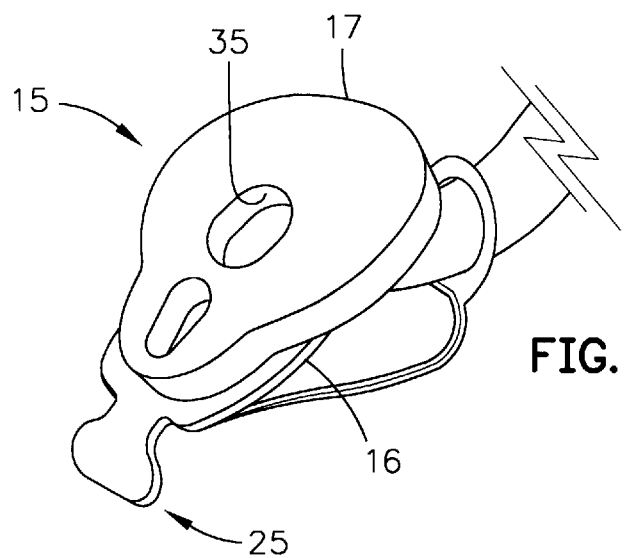

Further, the positioning elements may be applied singlely, or in any combination, to a sealing airway device, with embodiments as described or any equivalents thereof. Some examples are illustrated in FIGS. 19A–19C, where in FIG. 19A a laryngeal airway device is shown only with the lateral flanges 24; in FIG. 19B, only with the snout-like distal end 28*b* of the tubular extension 28; and in FIG. 19C with only the flexible flange 25.

Clearly, many other embodiments and modifications of this invention will occur readily to those of ordinary skill in the art in view of these teachings. Therefore, this invention is to be limited only by following claims, which include all such embodiments and modifications when viewed in conjunction with the above specification and accompanying drawings.

We claim:

1. A laryngeal airway device, comprising:
   an air tube with two ends;
   a sealing member mounted to the air tube, near one end of the tube, and including a distal end;
   an anterior surface on the sealing member;
   a passageway through the sealing member aligned with the one end of the tube and having an opening in the anterior surface;
   a pair of opposing lateral flanges extending from respective sides of the sealing member;
   a tubular extension at the one end of the tube disposed in the passageway and extending through the opening in the anterior surface; and
   a flexible flange on the sealing member near the distal end.

2. The device of claim 1, wherein the sealing member includes:
   a compressible pad, the anterior surface being a surface of the pad; and
   a support member with a contoured, anterior surface on which the pad is received, the contoured anterior surface having two sides, the lateral flanges extending upwardly from the sides, near the distal end.

3. The device of claim 2, wherein the flexible flange extends forwardly from the distal end and is rotatable toward and away from the tubular extension.

4. The device of claim 2, wherein the anterior surface of the support ember has a substantially sigmoid contour with a distal portion that forms an acute angle with the tubular extension.

5. The device of claim 4, wherein the tubular extension is a tubular section separate from the air tube, with a first end and a second end, the first end extending through the opening, beyond the anterior surface, and the second end receiving and retaining the one end of the air tube.

6. The device of claim 1, further including an arytenoid depression in the anterior surface positioned between the tubular extension and the distal end.

7. The device of claim 1 wherein the air tube has a curved shape with a portion that includes the one end of the tube and the anterior surface of the sealing member has a proximal end that forms an acute angle with the portion, defining a space therebetween.

8. The device of claim 1 wherein the tubular extension is a tubular section separate from the air tube, with a first and a second end, the first end extending through the opening, beyond the anterior surface, and the second end receiving and retaining the one end of the air tube.

9. The device of claim 1, wherein the sealing member has a posterior side, the device further including an inflatable member mounted on the posterior side of the sealing member.

10. A laryngeal airway device, comprising:

an air tube with two ends;

a sealing member mounted to the air tube, near one end of the tube, and including a distal end;

an anterior surface on the sealing member;

a passageway through the sealing member aligned with the one end of the tube and having an opening in the anterior surface;

a pair of opposing lateral flanges extending from respective sides of the sealing member; and a tubular extension at the one end of the tube disposed in the passageway and extending through the opening in the anterior surface.

11. A laryngeal airway device, comprising:

an air tube with two ends;

a sealing member mounted to the air tube, near one end of the tube, and including a distal end;

an anterior surface on the sealing member;

a passageway through the sealing member aligned with the one end of the tube and having an opening in the anterior surface;

a tubular extension at the one end of the tube disposed in the passageway and extending through the opening in the anterior surface; and a flexible flange on the sealing member near the distal end.

12. A laryngeal airway device, comprising:

an air tube with two ends;

a sealing member mounted to the air tube, near one end of the tube, and including a distal end;

an anterior surface on the sealing member;

a passageway through the sealing member aligned with the one end of the tube and having an opening in the anterior surface;

a pair of opposing lateral flanges extending from respective sides of the sealing member; and a flexible flange on the sealing member near the distal end.

13. A laryngeal airway device, comprising:

an air tube with two ends;

a sealing member mounted to the air tube, near one end of the tube, and including a distal end;

an anterior surface on the sealing member;

a passageway through the sealing member aligned with the one end of the tube and having an opening in the anterior surface; and a pair of opposing lateral flanges extending from respective sides of the sealing member.

14. A laryngeal airway device, comprising:

an air tube with two ends;

a sealing member mounted to the air tube, near one end of the tube, and including a distal end;

an anterior surface on the sealing member;

a passageway through the sealing member aligned with the one end of the tube and having an opening in the anterior surface; and a tubular extension at the one end of the tube disposed in the passageway and extending through the opening in the anterior surface.

15. A laryngeal airway device, comprising:

an air tube with two ends;

a sealing member mounted to the air tube, near one end of the tube, and including a distal end;

an anterior surface on the sealing member;

a passageway through the sealing member aligned with the one end of the tube and having an opening in the anterior surface; and a flexible flange on the sealing member near the distal end.

16. A sealing airway device, comprising:

an air tube with two ends;

a sealing member mounted to the air tube, near one end of the tube, and including a distal end;

a pair of opposing lateral flanges extending from respective sides of the sealing member; and a tubular extension at the one end of the tube and extending through the sealing member.

17. The sealing airway device of claim 16, further including a flexible flange on the sealing member near the distal end.

18. The device in claim 16, further including a proximal end on the sealing member that forms an acute angle with the air tube, defining a space therebetween.

19. A sealing airway device, comprising:

an air tube with two ends;

a sealing member mounted to the air tube, near one end of the air tube, and including a distal end;

a tubular extension at the one end of the tube and extending through the sealing member; and a flexible flange on the sealing member near the distal end.

20. A sealing airway device, comprising:

an air tube with two ends;

a sealing member mounted to the air tube, near one end of the tube, and including a distal end;

a pair of opposing lateral flanges near respective sides of the sealing member; and a flexible flange on the sealing member near the distal end.

21. The device of claim 20, wherein the sealing member has a proximal edge that forms an acute angle with the air tube defining space therebetween.

* * * * *